United States Patent
Krishnamoorthy et al.

(10) Patent No.: US 10,809,195 B2
(45) Date of Patent: Oct. 20, 2020

(54) OPTICAL DETECTION OF PARTICLES IN A FLUID

(71) Applicant: KONINKLIJKE PHILIPS N.V., Eindhoven (NL)

(72) Inventors: Ganeshram Krishnamoorthy, Eindhoven (NL); Joukje Garrelina Orsel, Valkenswaard (NL); Johannes Joseph Hubertina Barbara Schleipen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/064,507

(22) PCT Filed: Dec. 20, 2016

(86) PCT No.: PCT/EP2016/081831
§ 371 (c)(1),
(2) Date: Jun. 21, 2018

(87) PCT Pub. No.: WO2017/108733
PCT Pub. Date: Jun. 29, 2017

(65) Prior Publication Data
US 2018/0372634 A1 Dec. 27, 2018

(30) Foreign Application Priority Data
Dec. 23, 2015 (EP) .................................. 15202470

(51) Int. Cl.
*G01N 21/552* (2014.01)
*G01N 33/543* (2006.01)
(Continued)

(52) U.S. Cl.
CPC ..... *G01N 21/554* (2013.01); *G01N 33/54326* (2013.01); *G01N 33/54373* (2013.01);
(Continued)

(58) Field of Classification Search
CPC .............. G01N 21/554; G01N 33/553; G01N 33/54373; G01N 33/54326;
(Continued)

(56) References Cited

U.S. PATENT DOCUMENTS 6,280,960 B1 * 8/2001 Carr .................... G01N 15/1463
356/244
7,317,534 B2 1/2008 Kimura
(Continued)

FOREIGN PATENT DOCUMENTS

EP 0326375 A2 8/1989
WO 2003054566 A1 7/2003
(Continued)

OTHER PUBLICATIONS

Liedberg, Bo et al "Affinity Biosensing based on Surface Plasmon Detection", Methods in Biotechnology, vol. 7, Affinity Biosensors, 1998, pp. 31-53.
(Continued)

*Primary Examiner* — Hoa Q Pham

(57) ABSTRACT

A sensor platform (300) with a sensor surface (350) receives particles (400). A material extending from the sensor surface (350) having a refractive index higher than the one of the fluid (200), such that an electromagnetic wave (10) propagating in this platform material (310) and incident to the sensor surface (350) at an angle greater than the critical optical angle is totally reflected onto the sensor surface (350). The particles (400) suspended in the fluid (200) include a metallic material (410) enabling a localized surface plasmon resonance at resonant wavelength(s). An optical detector (102) detects a portion of a spectrum of the totally reflected wave (20), including the resonant wavelength(s). A processor determines a presence of the particles (400) on or close to the sensor surface (350) from a frustrated totally internal reflection ("FTIR") signal
(Continued)

retrieved from the detected wavelengths. The retrieving takes into account the detected resonant component(s) present in the FTIR signal.

20 Claims, 2 Drawing Sheets

(51) Int. Cl.
*B82Y 25/00* (2011.01)
*G01N 21/03* (2006.01)

(52) U.S. Cl.
CPC ...... *B82Y 25/00* (2013.01); *G01N 2021/0325* (2013.01); *G01N 2201/0221* (2013.01)

(58) Field of Classification Search
CPC ... G01N 2021/0325; G01N 2021/3595; G01N 2291/014
USPC ............... 356/445–448, 335–343; 324/244; 422/68.1
See application file for complete search history.

(56) References Cited

U.S. PATENT DOCUMENTS

| | | | | |
|---|---|---|---|---|
| 8,411,274 | B2* | 4/2013 | Verschuren | G01N 21/648 356/243.1 |
| 8,797,028 | B2* | 8/2014 | Verschuren | G01N 15/06 324/244 |
| 2005/0287681 | A1 | 12/2005 | Nishiuma | |
| 2006/0057384 | A1 | 3/2006 | Simard | |
| 2010/0164489 | A1 | 7/2010 | Lukaszew | |
| 2011/0027916 | A1* | 2/2011 | Nieuwenhuis | B01L 3/502761 436/526 |
| 2013/0141726 | A1 | 6/2013 | Van Lieshout | |
| 2013/0293896 | A1* | 11/2013 | Fujimaki | G01N 21/553 356/445 |
| 2014/0057366 | A1 | 2/2014 | Dittmer | |
| 2014/0209683 | A1 | 7/2014 | Schultz | |
| 2015/0060697 | A1* | 3/2015 | Umetsu | G01N 21/648 250/458.1 |
| 2015/0125873 | A1 | 5/2015 | Newman | |
| 2016/0079479 | A1* | 3/2016 | Yamana | H01L 51/5268 257/98 |

FOREIGN PATENT DOCUMENTS

| | | |
|---|---|---|
| WO | 2008072156 A2 | 6/2008 |
| WO | 2011006002 A2 | 1/2011 |
| WO | 2013072877 A1 | 5/2013 |

OTHER PUBLICATIONS

Kronick et al "New Immunoassay based on Fluorescence Excitation by internal-reflection spectroscopy", Journal Immunol. Methods, vol. 8, pp. 235-240, 1975.

Dreaden, Erik C. et al "Size matters: gold nanoparticles in targeted cancer drug delivery", Therapeutic Delicery, vol. 3, No. 4, 2012.

Shiigi, Hiroshi et al "Efficient Collection and Sensitive Detection Using Conducting Magnetic Microbeads", Analytical Chemistry, vol. 86, No. 10, 2014 pp. 4977-4981.

Kouassi, Gilles et al, "Magnetic and Gold-Coated Magnetic Nanoparticles as a DNA Sensor", Analytical Chemistry, vol. 78, No. 10, 2006, pp. 3234-3241.

* cited by examiner

OPTICAL DETECTION OF PARTICLES IN A FLUID

CROSS-REFERENCE TO PRIOR APPLICATIONS

This application is the U.S. National Phase application under 35 U.S.C. § 371 of International Application No. PCT/EP2016/081831, filed on Dec. 20, 2016, which claims the benefit of European Patent Application No. 15202470.9, filed on Dec. 23, 2015. These applications are hereby incorporated by reference herein.

FIELD OF THE INVENTION

The invention relates to sensing systems and methods allowing optical detection of particles in a fluid, in particular an organic fluid (e.g. blood, serum, plasma, saliva). The detection of those particles may be used for different purposes, such as a measurement of a state, physical, mechanical and/or chemical parameters of the liquid, or healthcare diagnosis in the event those particles are functionalized to specifically bind or react with some substances corresponding to this diagnostics, such as immunoassays or the detection of an (amplified) nucleic acid-containing molecule.

BACKGROUND OF THE INVENTION

From the different optical detections of particles in a fluid, Frustrated Total Internal Reflection ("FTIR") is known from WO2008/072156. FTIR comprises illuminating a sensor surface with an incident beam at an angle such that it is totally reflected thereon. An evanescent light field of several tens to few hundreds nanometers is formed accordingly on the sensor surface. Due to the presence of particles in this evanescent field, the totally reflected light becomes "frustrated". This decrease in totally reflected light is dependent on the number and optical properties of said particles. Particles may be kept at the sensor surface through various types of elements, for example biomaterials bonded to the sensor surface. Thus it is possible to relate the extent of frustration of the light to the concentration of said elements.

An alternative known optical detection is the surface plasmon resonance ("SPR")-type detection (B. Liedberg and K. Johansen, Affinity biosensing based on surface plasmon detection in "Methods in Biotechnology, Vol. 7: Affinity Biosensors: Techniques and Protocols", K. R. Rogers and A. Muchandani (Eds.), Humana Press Inc., Totowa, N.J., pp. 31-53), consisting of creating a surface plasmon resonance via a metallic layer coated on a transparent carrier (e.g. a prism), and detecting this resonance in a received signal. Depending on the mass and number of molecules present on the metallic surface, the net dielectric function or refractive index changes at the surface, and the detected SPR signal changes accordingly. Presence and relation to concentration of the molecules on the sensing surface can be then assessed.

Another alternative known optical detection involves the binding of each particle to be detected with an optical label (i.e. fluorescent label or dye), and to detect the light emitted by the characteristic feature of these optical labels and thus assess the presence and/or the number of molecules in the fluid. In particular, it is known to make use of evanescent wave excitation for a fluorescence immunoassay (Kronick and Little, 1975—"New immunoassay based on fluorescence excitation by internal-reflection spectroscopy" J. Immunol. Meth. 8, 235-240).

SUMMARY OF THE INVENTION

One of the main purposes of the invention is the enhancement of the sensitivity of the existing assays and/or optical detection systems.

Another purpose of the invention is the integration of such optical detection system in a handheld device, e.g. for point of care testing. This constraint further involves a non-cumbersome system, robust and reliable (i.e. which is still sufficiently accurate even if it is moved easily by hand from one place to another).

The inventors have indeed noticed that the plasmon resonance localized on the surface of metallic particles could be detected not only by bright field scattering (i.e. detecting the light scattered once the localized plasmon is excited) but also in the an FTIR system dedicated to detect specifically this localized plasmon resonance in the detected totally reflected wave.

A material that is used for the particles is a metallic material that enables a localized plasmon resonance at a resonant wavelength if excited at an excitation wavelength. The resonant wavelength is typically the same as the excitation wavelength. Metals for localized plasmon resonance usually have a good electrical conductivity, reflected in the availability of free conduction electrons, causing the material to have a negative real part of the dielectric constant (below the plasma frequency). In general noble metals are good conductors, but also other metallic materials show plasmonic effects, such as e.g. indium-tin-oxide (ITO). A non-exhaustive list of metal materials that can be used for the particles is hereby given: gold, silver, titanium, chromium, copper, ITO or indium-tin-oxide. This material can be provided in the bulk of the particles or can be coated on the surface of the latter. Such nanoparticles or microparticles in FTIR technology have the advantage of enhancing the assay sensitivity by an increased interaction of the particles with the evanescent field due to localized plasmon excitations at resonant wavelength(s), if excited at the excitation wavelength(s); this plasmonic signal resulting from the creation of localized plasmons on the surface of each particle around the resonant wavelength(s) or frequency(ies). Occurrence of such localized plasmon resonance leads to increased light scattering and/or absorption by the particle. This increased scattering and/or absorption will decrease the frustrated total internal reflected light around the resonant wavelength(s) by leading to an enhanced "negative" or "inverted" intensity. This negative intensity results in a decreased FTIR intensity (a drop in the reflected signal) directly due to presence of particles in the evanescent wave. The presence of this resonant information in the reflected light enhances the signature of the particle in the received FTIR signal, in comparison with a particle of the same size but which would not comprise any metallic material. This enhancement increases accordingly the probability of detecting the presence of said particle in the FTIR signal, and increases the sensitivity of the whole FTIR system.

Especially this FTIR system is arranged on the one hand to emit and transmit light with appropriate wavelengths to plasmonically excite the metallic surface of the particles at resonance frequency, and on the other hand to detect the information related to the localized plasmon resonance in the light reflected onto the sensor surface.

The detector of the invention may be further arranged to identify more specifically, in the reflected light, the low intensity(ies) related to the resonant wavelength(s) of the particle(s) to be detected, e.g. by being configured to have a high spectral-resolution around the resonant wavelength(s)

for the considered low intensity. In a particular embodiment, the detecting system of the invention has a prior knowledge of the resonant value(s) (frequency(ies) or wavelength(s)) of the particle(s) (such properties being mostly linked to the particle size and thickness of the metallic layer of material provided in the particle), stored in its memory, which may be used to help in identifying the resonance information in the FTIR signal.

Such detector may be a multispectral imaging sensor or camera, or a camera with tunable spectral filters (e.g. grating, prism, dielectric coatings).

Furthermore, it is to be noted that such an FTIR system may be seen as a particularly non-cumbersome system (especially in comparison with a bright field detection system) since it is positioned on only one side of the platform and with a tilted angle particularly beneficial for an integration in the housing of an analyzer.

Furthermore such FTIR system requires low-costs components, and requires low-NA, low magnification optics, resulting in a large field of view.

The detection arrangement of this system comprises a processor (or processing means), of hardware and/or software type, which is adapted to retrieve from the detected spectrum presence of said at least one particle, but taking into account the localized resonant components in the FTIR signal. These localized resonant components, identifiable in the FTIR signal, allow in particular the determination of the presence of the particles comprising some metallic material on or close to the sensor surface, especially by identifying the intensity of the resonant components or by determining a change in the reflected light (enhanced by the localized plasmon resonance). For instance, if the "negative" intensity is three times higher than the negative intensity that one can expect from a single particle, one can deduce that three particles have been detected.

The enhancement of the attenuation of the FTIR signal with the resonant components due to presence of particles improves therefore significantly the sensitivity of the sensing system, since signal to noise ratio is higher, so the probability to miss some particles in the detected signal is lower and so a lower number of particles can be detected in comparison with FTIR system of prior art.

The invention may open accordingly to new types of signal analyses based on lower amounts of particles to be detected, and thus to new applications.

Furthermore, the invention is about the detection of particles arranged to be diluted in the fluid (typically a liquid, e.g. a biological sample: blood, saliva, etc.). It means that the system stores such particles in such a way that, once the fluid is provided to the system (e.g. the fluid is a biological sample taken from a patient), the particles can move in the bulk of this fluid and therefore interact with some components of the fluid. These interactions in the volume of the sample are a very interesting aspect of the invention as they may enable many different applications. In particular, the surface of the particles might be provided with chemical components, enzymes, other biomaterials (e.g. antibodies, nucleic acids) provided with epitopes or sequences that specifically bind to or convert some analytes of the fluid. These multiplied interactions in the bulk of the fluid further enhance the reliability of the sensor and of its analysis, in comparison with a case where those particles (comprising a metallic material) would be bonded directly and fixedly onto the sensor surface and so be exposed only to the portion of the fluid in contact with the sensor surface. This is an actual difference with the known surface plasmon resonance ("SPR") sensor where binding can only take place two-dimensionally to the sensor surface.

After these particles are sufficiently incubated in the fluid, their presence onto or close to the sensor surface is detected. "Close to" means sufficiently close so as to be at least interact to some degree with the evanescent wave.

Said particle(s) can be put into contact with (or close to) the sensor surface by random Brownian motion, diffusion, sedimentation, gravitation or any other means.

Optionally, those particles comprise a magnetic material, or are bonded to a magnetic material, in particular a superparamagnetic material. In particular, the magnetic material can be included in the core of the particles and the metallic material provided along a continuous external surface of the particles. This magnetic material is arranged to provide the particles some magnetic properties (further to its plasmonic properties) sufficiently high to be magnetically manipulated in the fluid, if appropriately magnetically activated by a magnetic field externally supplied. This manipulation may be used to mix the particles in the fluid and enhance their interactions with some fluid substances. This activation may further or alternatively be used to attract and/or repulse the particles towards or away from the sensor surface. To this purpose, the system may further comprise a first magnetic source arranged to magnetically attract said at least one particle in the fluid to the sensor surface, and/or a second magnetic source arranged to magnetically repulse said at least one particle in the fluid away from the sensor surface. In a particular embodiment, said first and second magnetic sources are the same magnetic source operating in a first mode for the attraction and in a second mode for the repulsion. At least one of said magnetic source(s) may be positioned between the light emitter and light detector of the FTIR system, and the corresponding circuitry, so as to facilitate the integration of the overall system in the housing of an analyzer while allowing a reasonably small size for the analyzer, adaptable for a handheld use. Moreover, the overall arrangement of such an analyzer may be compact, rendering the assembly more robust.

As an option, the invention may be further arranged to implement an clinical chemistry, an immunoassay, clinical chemistry or a nucleic acid assay: to that purpose, said at least one particle may be further functionalized with a specific binder (e.g. an antibody, a nucleic acid, a binding protein or any other molecule or combination of molecules able to bind an analyte) or chemistry reactive (e.g. enzyme, a substrate, a coloring agent) to a target analyte (e.g. a protein, a nucleic acid, cells, virus, DNA, RNA, PNA, a lipid, a hormone or any other molecule or combination of molecules that is of interest) in the fluid. In that case, such particles can be further arranged to capture some fluid elements or to chemically react with some other elements to create a chemical change optically detectable, such that the detection of such particles on the sensor surface is correlated with the presence of those elements in the fluid. If those elements are representative of a disease or a probability of disease or malfunction of a patient, animal or other organism (from whom the fluid has been collected), the system of the invention can be a powerful and sensitive system for clinical or pre-clinical diagnostics. Other applications could be to investigate an organism or research model (e.g. cell culture, cell-free system and the like) to gain insight in diseases or other aspects of life sciences. In a more particular or alternative embodiment, the sensor surface may be further functionalized with specific bonds to a target analyte or to an analogue of the target analyte present in the fluid. This particular embodiment, together with the functionalization of the particles may lead to a sandwich or a competitive assay, well-known in the art. This assay will be detected with higher sensitivity thanks to the invention.

As an option, the invention can be further arranged such that said at least one particle comprising said metallic material, is stored in a dried assay before the fluid is provided to the system. This storage may be localized inside the platform, e.g. in a disposable, on or outside the sensor surface. The platform may be further adapted to drive the fluid to a detection chamber where the detection takes place, and to store the dried particles upstream of the detection chamber or inside the detection chamber. The storage of the particles in a dried format allows the platform to be stored, loaded with the embedded particles, ready to use. Alternatively or in combination, those particles may be stored in a wet format.

As a further option to the invention, the platform material may be arranged to be transparent to a narrow-band of the incident wave, around said at least one resonant wavelength. Alternatively or in combination, the detector and/or the processor may be provided with a narrow-band filter around said at least one resonant wavelength. This and/or the other embodiment(s) allows the system to retain only a portion of the FTIR signal around the localized plasmon resonant frequency. This embodiment can be interesting for improving the signal-to-noise ratio of the resonant signal from the remaining part of the FTIR signal. It can be used also to focus only on the localized resonance phenomena while filtering out any unwilling information outside the localized resonance. Alternatively or in combination of any of the foregoing, the light source of the system, or a filter upstream the light source, limits the incident light to a narrow-band around said at least one resonant wavelength.

The system may further comprise one or several other particles of a second type arranged to be diluted in the fluid too, and comprising a metallic material enabling a localized plasmon resonance at at least one second resonant wavelength(s) if excited at second excitation wavelength(s), and wherein said second resonant wavelength(s) is or are respectively different from said resonant wavelength(s). This difference of resonance wavelengths between these two particles may be due to the difference of (i) sizes and shape of, and/or (ii) thicknesses of metallic material coating provided onto, the particles of the two types. This option is particularly interesting for a system in which the use of two or more different kinds of particles enables the detection of two or more different analytes. In the above-mentioned particular case where the particles are functionalized to specifically capture or bind to analytes in the fluid, the system may be configured to detect different kinds of analytes. And according to an embodiment of the invention, there are different types of particles (i.e. having proper localized plasmon resonant values per type, as aforementioned), each type of particle being functionalized to allow for specifically binding or reacting with one type of analyte, such that, by detecting in the FTIR signal two different resonant signals and measuring their respective intensities, we can identify and distinguish two corresponding types of analytes and detect them accordingly (or determine their concentration) in the fluid. This embodiment may be implemented from the same initial waves (i.e. broadband light source) or from different incident waves emitted separately over time (i.e. tunable narrow-band light source). This embodiment allows thus to detect quickly and at low costs different analytes. This is a multiplex system. FTIR is particularly advantageous of use and adapted for such "multiplex" embodiment, since FTIR is typically detected over a large field of view (which is not the case for instance for bright-field microscopic detection geometries). The system may be arranged to detect two or more particles with different resonant wavelengths either at the same time or sequentially.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
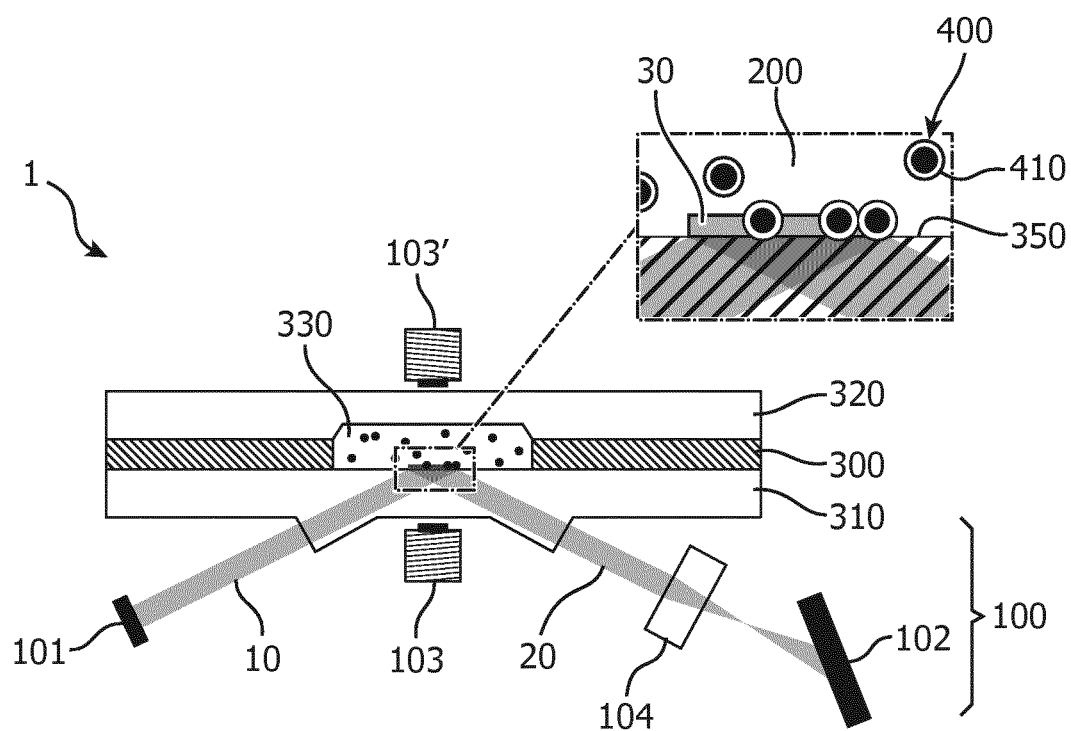
FIG. 1 shows a schematic side-view of an FTIR system.

FIG. 1 shows a schematic view of a known FTIR system 1, comprising a platform 300 embedding particles 400 and having a sensor surface 350, arranged to receive a fluid 200, and a reader 100. The platform 300 and the reader 100 are arranged to closely operate one to the other such that the reader 100 can send light to and receive light from the sensor surface 350 of the platform 300.

In particular, the reader 100 comprises:

a light emitter 101, e.g. at least one light emitting diode (LED), to emit a light beam or wave 10 onto the platform 300;

an arrangement to receive a sensor platform 300, such that the sensor surface 350 can receive the light emitted from the light emitter 101;

a light detector 102, e.g. a 2D camera, e.g. a CMOS camera tunable to detect different wavelengths or a multispectral camera, positioned to detect at least a portion of the reflected light 20, which has been reflected by the platform 300, optionally through a lens or a prism 104 or any other appropriate optical elements known by the person skilled in the art; generally speaking, the light emitter 101, said arrangement and the light detector 102 are configured and positioned one to the others such that light emitted by the light emitter 101 can be received by the sensor platform 300 positioned in the arrangement, and the light reflected by the sensor surface 350 is received by the light detector 102;

a processor (not shown) positioned downstream the detector 102 and arranged to determine a presence of said particles 400 based on information retrieved from the received light and related to a frustration of the totally internal reflected wave due to presence of particles 400, this retrieved information further including some localized plasmon resonant information of the particles 400; the processor may be provided in a single housing of the reader 100 (not shown), together with the light emitter 101, the light detector 102 and the magnetic source 103-103' (described hereafter), and/or in a docking station or local computer (not shown) in a proximate communication with the reader and/or in a remote location in communication with the reader 100 via a communication network.

magnetic source(s) 103-103' to generate a magnetic field in the fluid 200 to exert forces on the diluted particles 400, to the extent that those particles 400 comprise appropriate magnetic material (e.g. superparamagnetic material) and whose control allows the manipulation of the particles 400 inside the fluid 200, towards the sensor surface 350 and/or outwards from the sensor surface 350 and/or over more complexed motions.

The platform 300 may be a disposable, optionally mostly made of a polymer material or of any kind of material subject to the optical properties needed for implementing the invention.

The platform 300 comprises:
a base part 310 provided with a platform material transparent to at least certain wavelengths of the incident light 10, extending from and below the sensor surface 350;
optionally a cover 320, e.g. a laminate foil, positioned on the base part 310.

The base part 310 and/or the cover 320 may be configured to define microfluidic components between them, such as a detection chamber 330, microchannels, other chambers and structures, etc. to process the fluid 200 downstream and upstream the detection chamber 330 (not shown). A surface portion of the base part 310 and/or cover 320 may be used and configured to store some particles 400, preferably upstream or in the detection chamber 330, before the fluid 200 is provided for the detection purpose.

The refractive index n1 of said platform material is higher than the refractive index n2 of the fluid 200 so as to define an optical critical angle $\theta_c$ from the normal of the sensor surface 350 such that an electromagnetic wave 10 propagating in this platform material and incident to the sensor surface 350 at an angle $\theta_i$ greater than the critical optical angle $\theta_c$ is totally reflected onto the sensor surface 350. As well-known, the consequence of this total reflection is the creation of an evanescent wave 30, typically from tenths to a few hundred nanometers height on the sensor surface 350.

The light emitter 101, the light detector 102 and the platform 300 are configured and positioned one to the others such that, indeed, the incident light 10 is reflected onto the sensor surface 350 and the reflected light 20 is received by the light detector 102.

The particles 400 may be stored in a dried state, as above-mentioned, and are arranged to be suspended in the fluid 200 (typically a liquid, e.g. a biological sample: blood, saliva, etc.). Once the fluid 200 is provided to the system 1 (e.g. the biological sample is taken from a patient), the particles 400 can move in the bulk of this fluid 200 and therefore interact with some components of the fluid 200. The particles 400 are provided with a metallic material (e.g. gold, silver) such that a localized resonant plasmon 40 is generated once excited by the incident light 10, at the proper resonant wavelength. This metallic material can be provided in the bulk of the particles 400 or provided as a continuous layer 410 on the surface of the particles 400. The size of the particle 400 and the thickness of the layer 410 for the considered chosen metal will mostly determine the resonance wavelength(s) of the localized plasmon.

Those particles 400 further comprise a magnetic material, or are bonded to a magnetic material, in particular a superparamagnetic material. This magnetic material can be included in the core of the particles 400 and the metallic material is provided along a continuous external surface of such particles 400. In particular this magnetic material is arranged in the particle(s) 400 in such a way that, if appropriately activated by the magnetic field supplied to it by the magnetic source(s) 103-103', the particle(s) 400 can be magnetically manipulated in the fluid 200.

Figure 2:
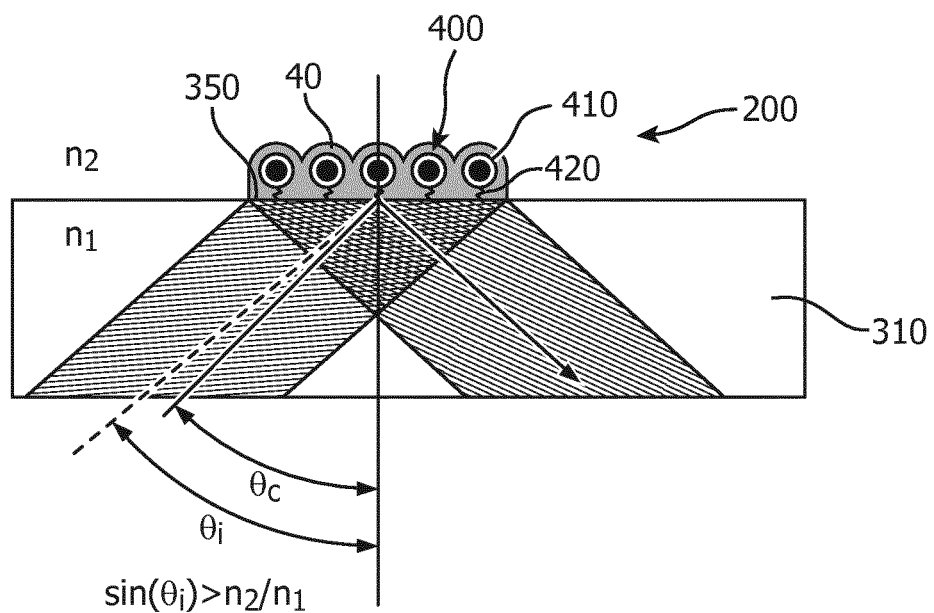
FIG. 2 shows a sensor surface of an FTIR system in operation according to the invention.

The surface of the particles 400 might be further provided or functionalized with chemical components, enzymes, other biomaterials (e.g. antibodies, nucleic acids, a binding protein or any other molecule or combination of molecules able to bind an analyte) provided with epitopes/receptors or sequences that specifically bind to analytes (e.g. a protein, a nucleic acid, cells, virus, DNA, RNA, PNA, hormone, lipid or any combination or conjugation of two or more of these analytes) of the fluid 200. In addition or alternatively, the sensor surface 350 may be functionalized with specific bonds to a target analyte or to an analogue of the target analyte in the fluid. This particular embodiment, together with the functionalization of the particles 400 may lead to a sandwich (or alternatively a competitive assay, not shown here), well-known in the art, as depicted by the bonds 420 in FIG. 2, such that the amount of bound particles can be related to the concentration or activity of the analyte.

The platform material of the platform 310 may be arranged to be transparent to only a narrow-band of the spectrum of the incident wave 10, around said resonant wavelength(s) of the particles 400. For example, the platform material may be a material leaving only the blue light going through it knowing that the resonant wavelength of the particles 400 is in the blue spectrum. This embodiment may be interesting for filtering out some unwilling wavelengths or discarding the resonance of other types of particles 400 (for example when some particles 400 of the other types have a localized resonance in the red spectrum).

Alternatively or in combination, the detector 102 and/or the processor may be provided with a narrow-band filter around said at least one resonant wavelength of particles 400. This and/or the other embodiment(s) allows the system 1 to retain only a portion of the FTIR signal around the wavelength corresponding to the localized resonant plasmon. This embodiment can be interesting to improve the signal-to-noise ratio of the resonant signal from the remaining part of the FTIR signal. It can be used also to focus only on the localized resonant phenomena while filtering out any unwilling information outside the localized resonance.

As already indicated, the system may comprise particles 400 of different types, each type enabling a proper localized plasmon resonance, i.e. having a proper resonant wavelength(s) for excitation. In the above-mentioned particular case where the particles are functionalized to specifically capture or bind with analytes in the fluid, one kind of analyte per kind of particles, the different kinds of analytes may be clearly identified and detected thanks to the invention, by detecting in the FTIR signal the different corresponding resonant signals in the FTIR spectrum and measuring their respective intensities. This embodiment may be implemented from the same initial waves 10 or from different incident waves 10 emitted separately over time.

Figure 3:
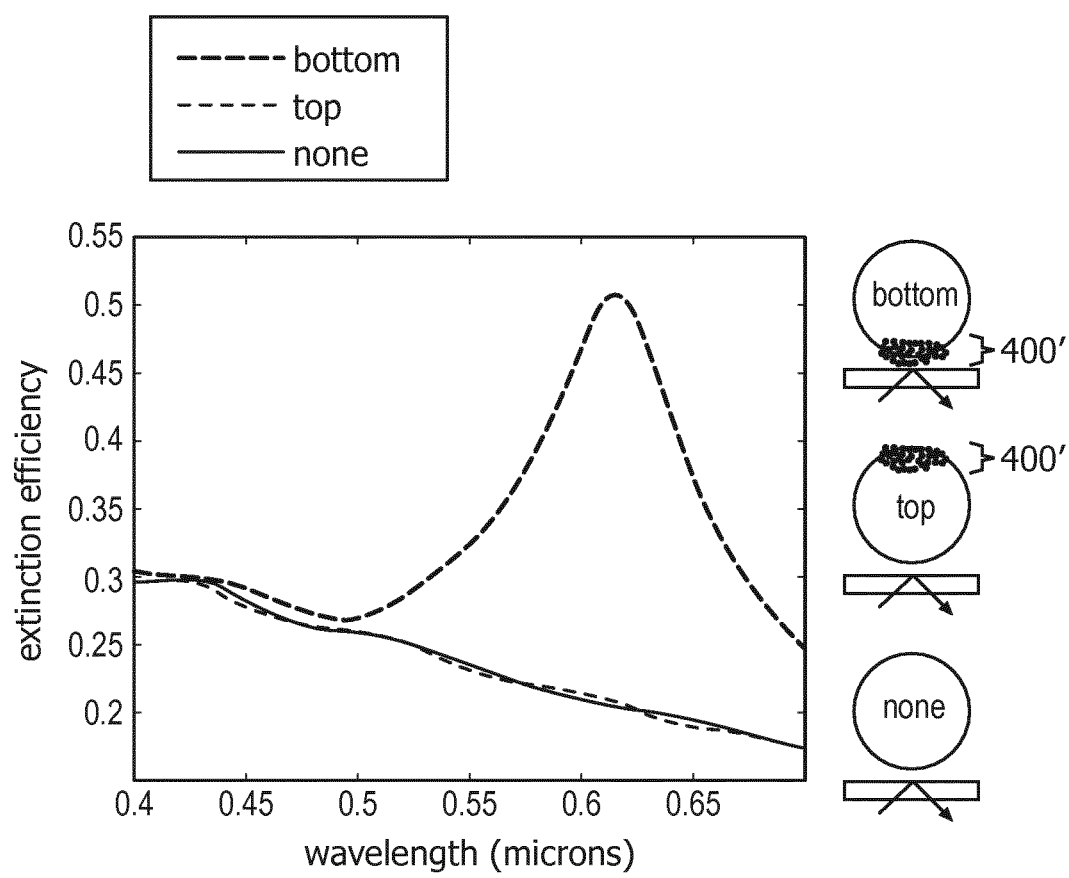
FIG. 3 shows a scattering simulation result of 500 nm magnetic beads with 50 nm gold particles coating, lighted through a Philips Minicare platform, in a blood sample.

FIG. 3 shows how a resonant signal can be detected here the resonant wavelength of the considered particles 400 is around 0.62 micrometers and whose detection also depends on the distance of the particles 400 from the sensor surface 350, i.e. the presence of the particles in the evanescent wave 30. This figure has been obtained from optical scattering simulations where a magnetic particle has been placed inside an evanescent field, with ("bottom") and without ("top") a metallic gold coating. Here the "top"-labeled curve depicts the overall extinction (scattering and absorption) efficiency where the metallic coating is outside the evanescent field and no plasmonic effects are to be expected. The "bottom"-labeled curve illustrates the effect of plasmon excitation where the total extinction efficiency increases by a factor of 3 (in this specific example), which will be reflected by a corresponding increase in reduction or frustration of the FTIR signal.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. For instance, the system of the invention can be used not only with the particles according to the invention, but being used with other types of particles in combination with the particles of the invention.

The invention claimed is:

1. A system for optically detecting at least one particle in a fluid, comprising:
   a sensor platform comprising:
      a sensor surface;
      a platform material,
      wherein the platform material extends from the sensor surface,
      wherein platform material is transparent to an excitation wavelength(s) and at least one first resonant wavelength(s),
      wherein platform material has a refractive index higher than a fluid refractive index,
      wherein the refractive index is defined according to as a refractive angle from the normal of the sensor surface,
      wherein an electromagnetic wave propagating in this platform material and incident to the sensor surface at the refractive angle is totally reflected onto the sensor surface when the refractive angles greater than the critical optical angle;
   an optical detector,
      wherein the optical detector is arranged to detect at least a portion of the spectrum of the electromagnetic wave which has been totally reflected onto the sensor surface,
      wherein the optical detector is arranged to generate a frustrated totally internal reflection (FTIR) signal,
      wherein the portion of the spectrum includes the at least one first resonant wavelength(s);
   a processor circuit,
      wherein the processor circuit is arranged to determine a presence of the at least one particle on or close to the sensor surface from the FTIR signal,
      wherein the determining uses the plasmon resonance wavelength(s) present in the FTIR signal,
   wherein the at least one particle is stored before the fluid is supplied to the system,
   wherein the at least one particle is arranged to be suspended in the fluid,
   wherein the at least one particle comprises a metallic material,
   wherein the metallic material enables a plasmon resonance at least one first resonant wavelength(s) if excited at the excitation wavelength(s),
   wherein the fluid has the fluid refractive index.

2. The system of claim 1, wherein the at least one particle comprises a superparamagnetic material.

3. The system of claim 2, further comprising a magnetic source, wherein the magnetic source is arranged to magnetically attract the at least one particle to the sensor surface.

4. The system of claim 2, further comprising a magnetic source, wherein a second magnetic source arranged to magnetically repulse the at least one particle away from the sensor surface.

5. The system of claim 1, wherein the at least one particle is functionalized with a specific bond or chemistry reactive to a target analyte in the fluid.

6. The system of claim 1, further comprising a disposable,
   wherein the at least one particle is stored in the disposal, before the fluid is provided,
   wherein the disposable further comprises the sensor platform and platform material.

7. The system of claim 1, wherein the platform material is arranged to be transparent to a narrow-band of the incident wave around the at least one first resonant wavelength.

8. The system of claim 1, further comprising at least one second particle,
   wherein the at least one second particle is arranged to be diluted in the fluid,
   wherein the at least one second particle comprises a metallic material,
   wherein the metallic material enables a plasmon resonance at least one second resonant wavelength(s) if excited at second excitation wavelength(s),
   wherein the second resonant wavelength(s) is respectively different from the first resonant wavelength(s).

9. The system of claim 8,
   wherein system is arranged to detect two or more particles,
   wherein each particle has different resonant wavelengths.

10. The system of claim 8,
    wherein the system is arranged to detect two or more particles,
    wherein the detection of the two or more particles occurs at the same time.

11. The system of claim 8,
    wherein the system is arranged to detect two or more particles,
    wherein the detection of the two or more particles occurs at sequentially.

12. The system of claim 1,
    wherein the processor circuit is arranged to identify the at least one plasmon resonance wavelength(s),
    wherein the at least one plasmon resonance wavelength(s) is a, plasmon resonance in the FTIR signal,
    wherein the processor circuit is arranged to analyze the FTIR signal including the plasmon resonance wavelength(s) to determine the presence of the at least one particle.

13. The system of claim 1, wherein the sensor surface is functionalized with specific bonds to a target analyte or to an analogue of the target analyte in the fluid.

14. The system of claim 1, wherein the detector limits the incident light to a narrow-band around the at least one first resonant wavelength.

15. An analyzer for optically detecting presence of particles in a fluid, comprising:
    an optical source;
    an arrangement,
       wherein the arrangement is configured to receive a platform,
       wherein the platform is embedded with the fluid to be analyzed,
       wherein a transparent wall extends from a sensor surface of the platform,
       wherein the transparent wall is adjacent to the fluid wherein the transparent wall is illuminated by an electromagnetic wave emitted by the optical source;

an optical detector,
wherein the optical detector is configured and such that a light emitted by the optical source is received by the platform, and
wherein the light reflected by the platform is received by the optical detector; and a processor circuit,
wherein the processor circuit is arranged to determine a presence of the at least one particle on or close to the sensor surface from a frustrated totally internal reflection ("FTIR") signal,
wherein the determining takes into account detected resonant component(s) present in the FTIR signal linked to plasmon resonance,
wherein the plasmon resonance is localized on particles diluted in the fluid and located on or close to the transparent wall.

16. A method for optically detecting presence of at least one particle in a fluid, comprising:
providing a sensor platform,
wherein the sensor platform comprises a sensor surface over a transparent medium,
wherein at least one particle is suspended in the fluid,
wherein the at least one particle comprises a metallic material, wherein the metallic material enables a plasmon resonance at least one first resonant wavelength(s) if excited at an excitation wavelength(s);

providing the fluid to the sensor platform, wherein the refractive index of the fluid is lower than the refractive index of the transparent material;

illuminating the sensor surface with an incident light through the transparent material such that the incident light is totally reflected onto the sensor surface, wherein the spectrum of the incident light comprises the excitation wavelength(s) of the at least one particle(s);

detecting at least a portion of the spectrum of the incident light, wherein the portion of the spectrum includes the at least one first resonant wavelength(s);

determining a presence of the at least one particle on or close to the sensor surface from the frustrated totally internal reflection ("FTIR") signal, wherein the determining takes into account the plasmon resonance component(s) present in the FTIR signal.

17. The method of claim 16, wherein the detection is implemented such that two or more particles with different resonant wavelengths can be detected at the same time.

18. The method of claim 16, wherein determining the presence of the at least one particle includes determining the plasmon resonance wavelength(s) in the FTIR signal.

19. The method of claim 16, wherein the detection is implemented such that two or more particles with different resonant wavelengths can be detected sequentially.

20. The method of claim 16, further comprising magnetically attracting the at least one particle to the sensor surface.

* * * * *